United States Patent [19]

Moore

[11] 3,932,660
[45] Jan. 13, 1976

[54] INSECTICIDAL PHENYLHYDRAZONE SULFIDES

[75] Inventor: Joseph E. Moore, Richmond, Calif.

[73] Assignee: Gulf Research & Development Company, Pittsburgh, Pa.

[22] Filed: Jan. 27, 1975

[21] Appl. No.: 544,150

Related U.S. Application Data

[62] Division of Ser. No. 470,481, May 16, 1974, Pat. No. 3,867,449.

[52] U.S. Cl. ............................................... 424/327
[51] Int. Cl.². ........................................... A01N 9/20
[58] Field of Search .................................... 424/327

[56] References Cited
OTHER PUBLICATIONS
Chemical Abstracts, 77:88470b, (1972).

Primary Examiner—Leonard Schenkman

[57] ABSTRACT

Phenylhydrazone sulfides of the formula:

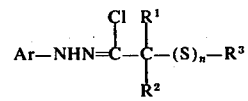

wherein $R^1$ and $R^2$ individually are hydrogen or alkyl, $R^3$ is alkyl, haloalkyl or phenyl substituted with up to 3 halogens, to 5 halogens, Ar is phenyl substituted with up to 5 halogens, and n is 1, 2 or 3, have morphogenetic hormonal mimetic insecticidal activity.

24 Claims, No Drawings

INSECTICIDAL PHENYLHYDRAZONE SULFIDES

This is a division of application Ser. No. 470,481, filed May 16, 1974, now U.S. Pat. No. 3,867,449.

BACKGROUND OF THE INVENTION

1. Field of the Invention

The present invention is concerned with insecticidal compounds which have morphogenetic hormonal mimetic activity. Compounds having morphogenetic hormonal mimetic activity exert a disrupting influence upon the normal development of insects. These compounds interfere with the normal metamorphosis of the pest insects and result in the formation of individual insects of the treated species which develop abnormally and are nonviable or sterile. This ultimately leads, indirectly at least, to the destruction of the insect population.

2. Description of the Prior Art

Thioketal-substituted phenylhydrazones are disclosed by M. W. Moon et al, "J. Arg. Food Chem.," 20, 888 (1972). German Pat. No. 2,157,601 [C.A. 77 88470b (1972)] also disclose thio-substituted phenylhydrazones. Phenylhydrazone compounds are also disclosed in "J. Agr. Food Chem.," 20, 1187 (1972); "J. Org. Chem.," 37, 383, 386, 2005 (1972); and Netherlands Pat. application No. 7,113,497.

DESCRIPTION OF THE INVENTION

The insecticidal phenylhydrazone sulfides of the invention are represented by the formula:

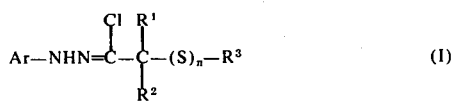

(I)

wherein $R^1$ is hydrogen or alkyl or 1 to 6 carbon atoms, $R^2$ is hydrogen or alkyl of 1 to 6 carbon atoms, $R^3$ is alkyl of 1 to 6 carbon atoms, haloalkyl of 1 to 6 carbon atoms and 1 to 5 fluoro, chloro or bromo groups or phenyl substituted with up to 3 (0 to 3) fluoro, chloro or bromo, Ar is phenyl substituted with up to 5 (0 to 5), more preferably with up to 3 (0 to 3), fluoro, chloro or bromo and $n$ is 1, 2 or 3.

Representative alkyl groups which $R^1$, $R^2$ and $R^3$ may represent include methyl, ethyl, n-propyl, isopropyl, n-butyl, sec-pentyl and isohexyl. Representative haloalkyl $R^3$ groups include trifluoromethyl, chloromethyl, trichloromethyl, 1,1,2,2-tetrachloroethyl, pentabromoethyl, pentachloroethyl, 4-chlorobutyl, etc. Representative halophenyl $R^3$ groups include 4-fluorophenyl, 4-chlorophenyl, 3-bromophenyl, 2,4-dichlorophenyl, and 2,4,6-trichlorophenyl. Representative halophenyl Ar groups include 2-fluorophenyl, 4-fluorophenyl, 4-chlorophenyl, 2,4-dichlorophenyl, 3,5-dichlorophenyl, 2,4-dibromophenyl, 2,4,6-tribromophenyl and pentachlorophenyl.

The preferred $R^1$ and $R^2$ groups are alkyl of 1 to 3 carbon atoms. The preferred $R^3$ group is alkyl of 1 to 6 carbon atoms, haloalkyl of 1 to 2 carbon atoms and 1 to 5 chloro or bromo, or phenyl or up to 3 chloro or bromo. The most preferred $R^3$ group is alkyl of 1 to 6 carbon atoms. The preferred Ar groups are phenyl and phenyl substituted with 1 to 5 chloro or bromo groups.

Representative compounds of formula (I) are tabulated in Table I ($\phi$ represents phenyl).

TABLE I

| Ar | $R^1$ | $R^2$ | $R^3$ | n |
|---|---|---|---|---|
| $\phi$ | H | H | $CH_3$ | 1, 2 or 3 |
| $\phi$ | $CH_3$ | H | $CH_3$ | " |
| $\phi$ | $C_2H_5$ | $CH_3$ | $CH_3$ | " |
| 2—F$\phi$ | $C_2H_5$ | $C_2H_5$ | $ClCH_2$ | " |
| 3—Cl$\phi$ | i—$C_3H_7$ | i—$C_3H_7$ | $Cl_2CH$ | " |
| 4—Br$\phi$ | $CH_3$ | n—$C_4H_9$ | $CCl_3$ | " |
| 2,4—$F_2\phi$ | $CH_3$ | n—$C_2Cl_5$ | | " |
| | $C_5H_{11}$ | | | |
| 3,4-$Cl_2\phi$ | $CH_3$ | n—$C_6H_{13}$ | $CH_3$ | " |
| 3,5—$Br_2\phi$ | $CH_3CH_3$ | $CH_3$ | | " |
| 2,4,6—$F_3\phi$ | $CH_3$ | $CH_3$ | $CCl_3$ | " |
| 2,4,6—$Cl_3\phi$ | $C_2H_5$ | $CH_3CH_3$ | | " |
| 2,4,6—$Br_3\phi$ | $CH_3$ | $CH_3$ | $CH_3$ | " |

A class of preferred phenylhydrazone sulfides of formula (I) are those wherein $R^1$ and $R^2$ individually are alkyl of 1 to 3 carbon atoms, $R^3$ is alkyl of 1 to 6 carbon atoms, chloroalkyl of 1 to 2 carbon atoms and 1 to 5 chloro, or phenyl of up to 2 chloro or bromo, Ar is phenyl substituted with up to 5 chloro, bromo or fluoro, more preferably phenyl substituted with up to 5 chloro, and $n$ is 1, 2 or 3.

The compounds of the invention wherein n is 2 or 3 may be prepared by reacting a bishydrazone (II) with excess chlorine and then reacting resulting sulfenyl chloride (III) with a mercaptan as depicted in the following reactions (1) and (2):

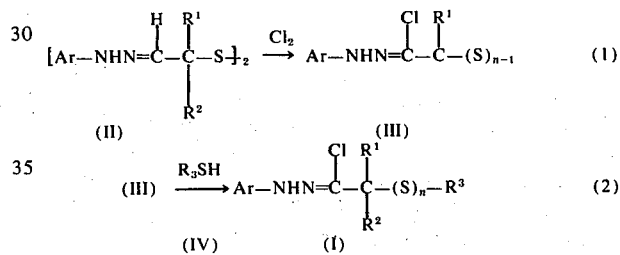

wherein $n$ is 2 or 3, and $R^1$, $R^2$, $R^3$ and Ar have the same significance as previously defined.

Reaction (1) is conducted with about 2 to 11 mols, preferably 3 mols to 3.5 mols, of chlorine per mol of the bis-hydrazone (II) in an inert solvent, e.g., chlorinated hydrocarbons such as methylene chloride and carbon tetrachloride, at a temperature of 0° to 50°C. The resulting sulfenyl chloride (III) may be isolated and purified. However, it is generally more convenient to react the sulfenyl chloride (III), without purification, with a substantially equimolar amount of the mercaptan (IV) at a temperature of 0° to 50°C. to produce the product (I). The product (I) is isolated and purified by conventional procedures such as extraction, filtration, crystallization and chromatography.

The compounds of the invention wherein n is 1 to 2 are prepared by reacting a hydrazide sulfide (V) which phosphorus pentachloride as depicted in reaction (3):

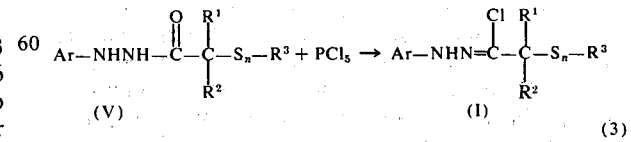

(3)

wherein $n$ is 1 or 2, and $R^1$, $R^2$, $R^3$ and Ar have the same significance as previously defined.

Reaction (3) is conducted by reacting substantially equimolar amounts of the hydrazide sulfide (V) and phosphorus pentachloride in the presence of an inert solvent at a temperature of about 0° to 100°C., and then working up the product mixture with phenol. Reaction (3) is a known reaction for the chlorination of hydrazides, as disclosed in Netherlands Pat. application No. 7,113,497.

The hydrazide sulfide reactant (V) is suitably prepared by reacting substantially equimolar amounts of an aryl hydrazide (VI) and an alkanoyl halide in the presence of an acid acceptor in an inert solvent at 0° to 50°C., as depicted in reaction (4):

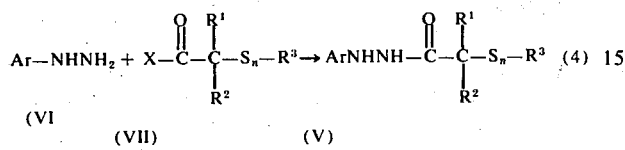

wherein $n$ is 1 to 2, X is chloro or bromo, and $R^1$, $R^2$ $R^3$ and Ar have the same significance as previously defined.

The hydrazide monosulfide reactant (V) ($n = 1$) is also suitably prepared by alkylating a bromo-hydrazide of the formula

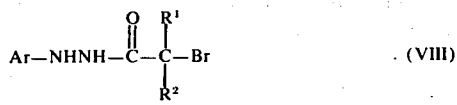

with an alkali metal mercaptide of the formula $R^3SM$ wherein M is an alkali metal and $R^1$, $R^2$, $R^3$ and Ar have the same significance as previously defined. The bromo-hydrazide reactant (VIII) is suitably prepared by reacting the aryl hydrazine (VI) and an alpha-bromoalkanoyl halide.

The compounds of the invention are useful as morphogenetic hormonal mimetic insecticides, particularly, against insects such as cabbage looper larvae, alfalfa weevil larvae, yellow mealworm, kissing bug and mosquitos.

The compounds are very potent and are used at extremely low concentrations. For example, compositions containing 100 ppm to 0.01 ppm, preferably from 5 ppm to 0.1 ppm, are effective for inhibiting or interfering with the normal metamorphosis of insects. However, the effective concentration depends in part on the mode of application and the particular insect.

The compounds may be applied in either liquid or solid formulations to the pre-adult insects or their habitats. For example, they may be sprayed or otherwise applied directly to plants or aqueous bodies so as to effect control of insects coming into contact therewith.

Formulations of the compounds of this invention will comprise a metamorphosis-inhibiting amount of one or more of the compounds and a biologically inert carrier. Usually they will also contain a wetting agent. Solid carriers such as clay, talc, sawdust, alfalfa meal, and the like may be used in such formulations. Liquid diluents which may be used with these compounds include water aliphatic and aromatic solvents. In addition, these formulations may contain other compatible pesticides, fillers, stabilizers, attractants and the like.

The concentration of the active ingredient to be used with inert carriers, either solid or liquid carriers, will be dependent upon many factors, such as the particular compound which is used, the carrier in or upon which it is incorporated, the method and conditions of application, the insect species to be controlled, etc., the proper consideration of these factors being within the skill of those versed in the art. In general, the toxic ingredients of this invention will be effective in concentrations from about 0.0001 percent by weight to as high as 50 percent by weight or higher. Economically, of course, it is desirable to use lower concentrations of this active ingredient.

The compounds of the invention are particularly useful in combination with mosquito larvicidal petroleum oil dispersions. Petroleum oils suitable as mosquito larvicidal dispersions are known. Such hydrocarbon oils include mineral oils such as naphthenic base and paraffinic base lubricating oils, etc., as well as synthetic oils. Such hydrocarbons oils are non-phytotoxic and generally contain not more than a few percent aromatics. Particularly suitable hydrocarbon oils have boiling points above 350° to 400°F. and viscosities of from about 33 to 200 SSU at 100°F.

The amount of the compound of the invention employed in petroleum oil generally ranges from 0.1 to 10 percent by weight based on weight of oil. The hydrocarbon oil dispersions containing the compounds of the invention are contacted with or applied to the surface of the aqueous bodies wherein mosquito control is desired by conventional methods.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insecta but also to other related classes of arthropods whose members are segmented invertebrates having more or fewer than six legs, such as spiders, mites, ticks, centipedes, worms and the like.

EXAMPLE 1

A mixture of 21.2 g. of 2,4,6-trichlorophenylhydrazine, 10.3 g. 2,2'-dithiobisisobutyraldehyde and 100 ml. ethanol was heated to reflux and filtered hot. The solvent was evaporated to leave a solid. The solid was washed with 50 ml. hexane and filtered to give 17.6 g. of the bis-hydrazine product, m.p. 85°–110°C. Recrystallization from hexane and then from ethanol gave the product as a white solid, m.p. 116°–117°C. Elemental analysis for $C_{20}H_{20}Cl_6N_4S_2$ gave: %s calc. 10.8, found 10.8; %Cl calc. 35.9; found 34.5.

To a cooled (0°C) and stirred mixture of 8.0 g. of the bis-2,4,6-trichlorophenylhydrazone of 2,2'-dithiobisisobutyraldehyde (prepared above) was added 3.3 g. chlorine in 50 ml. carbon tetrachloride over a 30-minute period. The mixture was filtered and the excess chlorine was removed under reduced pressure. To the reaction mixture was added 2 g. methyl mercaptan. The solvent was then stripped to leave 9.7 g. of a red oil. Nuclear magnetic resonance sprectroscopy showed that the oil was a mixture of hydrazone sulfides of the formula:

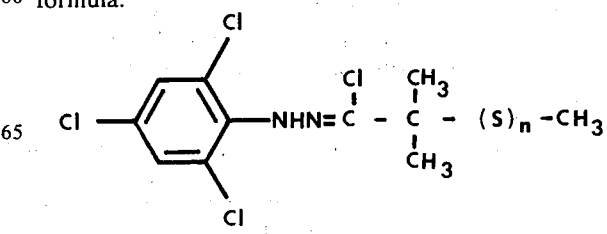

wherein n is 2 or 3.

The oil was chromatographed on silica gel (hexane eluant) to give a product (3.1 g.) consisting predominantly of the hydrazone trisulfide (n equal to 3). Sulfur analysis for the product was 19.0% and chlorine analysis for the product was 38.5 percent.

EXAMPLE 2

A solution of 3.3 g. chlorine in 50 ml. carbon tetrachloride was added dropwise over a 30-minute period to a cooled (0°C) and stirred mixture of 8.0 g. of the bis-2,4,6-trichlorophenylhydrazone of 2,2′-dithiobisisobutyraldehyde in 100 ml. carbon tetrachloride. The reaction mixture was filtered to remove a little solid material and then partially evaporated to remove excess chlorine. A 2.4 g. sample of 2-methyl-2-propanethiol was added and the resulting solution stirred for one hour at about 25°C. The solvent was then stripped to leave 10.4 g. of a red oil. The oil was chromatographed on silica gel (hexane eluant) to give 2.6 g. the hydrazone trisulfide of the formula:

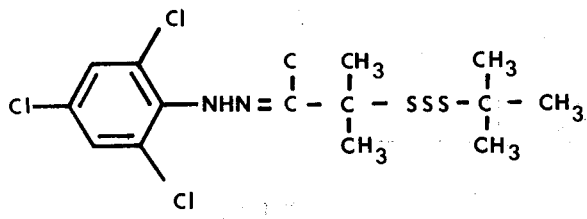

Elemental analysis for $C_{14}H_{18}Cl_4S_3$ showed: %S calc. 21.8, found 21.2; % Cl calc. 30.9, found 31.4. The hydrazone trisulfide was a red oil which solidified on standing to a low melting red solid.

EXAMPLE 3

A 24 g. sample of chlorine was bubbled into a mixture of 14.5 g. of the bis-phenylhydrazone of 2,2′-dithiobisisobutyraldehyde over a one-hour period. After stirring at about 25°C. for three hours, 5 g. of ethanethiol were added and the resulting solution stirred overnight. The solvent was then stripped to leave a red oil. The oil was chromatographed on silica gel (benzene eluant) to give 15 g. of a red oil. Nuclear magnetic resonance spectroscopy and elemental analysis (found 12.6%S, 37.2%Cl) showed the product to be a mixture of hydrazone sulfides of the formula:

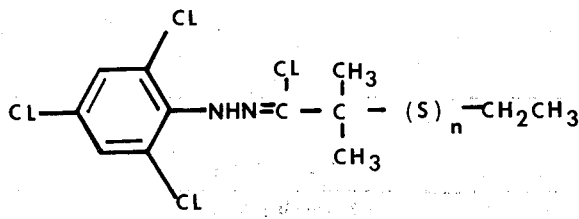

wherein n is 2 or 3.

The hydrazone disulfide (n = 2) was the predominant product.

EXAMPLE 4

A 23-g sample of 2-bromo-2-methylpropionyl bromide was added dropwise to a cooled (0°C). slurry of 21.2 g 2,4,6-trichlorophenylhydrazine and 7.9 g pyridine in 500 ml glyme over a 2-hour period. The reaction mixture was stirred ½ hour and poured into 500 ml ice water and 20 ml concentrated hydrochloric acid. A solid separated. The solid was filtered, washed with water and dried to give 27.3 g of the bromohydrazide product (Formula VIII where Ar is 2,4,6-trichlorophenyl and $R^1$ and $R^2$ are methyl) as a beige solid, m.p. 101°–103°C.

Sodium mercaptide was prepared by bubbling methyl mercaptan into a slurry of 5.5 g sodium hydride (54% in mineral oil) in 150 ml dimethylformamide. The sodium mercaptide solution was then cooled in an ice water bath while 44.9 g of the bromo-hydrazide prepared above in 100 ml dimethylformamide was added over a one-hour period. After stirring for 15 minutes, 150 ml benzene and 300 ml ice water were added. The benzene layer was separated, washed with water, dried over magnesium sulfate and evaporated to give a solid. The solid was crystallized from 100 ml boiling hexane to give 38.3 g of the mercapto-hydrazide product (Formula V where Ar is 2,4,6-trichlorophenyl, $R^1$, $R^2$ and $R^3$ are methyl and n is 1) as a beige solid, m.p. 85°–89°C.

A solution of 22 g of the mercapto-hydrazide prepared above and 14 g phosphorus pentachloride in 100 ml carbon tetrachloride was stirred at about 25°C. for 2 days and then refluxed for 30 minutes. The reaction was then cooled (0°C.) and 18.9 g phenol was added in one portion. The reaction mixture was then stirred at 25°C. for 5 days. 25 ml of methanol was added to the reaction mixture and the resulting solution was stripped to give an oil. The oil was chromatographed on silica gel (benzene/hexane eluant) to give 10.2 g of an orange oil which solidified on standing to an orange solid. Recrystallization from hexane gave 6.4 g of the hydrazone sulfide product, m.p. 51°–52°C, of the formula

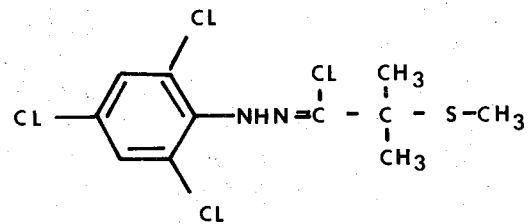

Elemental analysis showed: %S, calc. 9.3, found 9.4; %Cl, calc. 41.0, found 41.0.

EXAMPLE 5

A solution of 16.4 g 2-methyldithio-2-methylpropionic acid and 25 ml thionyl chloride was stirred and refluxed for 1 hour. The reaction mixture was then distilled to give 10.5 g of 2-methyldithio-2-methylpropionyl chloride, b.p. 100°–122°C. at 55 mm of Hg.

The 10.5-g sample of propionyl chloride prepared above was added dropwise over a 10-minute period to 12 g 2,4,6-trichlorophenylhydrazine and 6 g triethylamine in 250 ml glyme. After stirring for 10 minutes, 200 ml ice water and 10 ml concentrated hydrochloric acid were added. On stirring in an ice bath, a solid separated. The solid was filtered, washed with water, dried and recrystallized from hexane to give the hydrazide product (Formula V, where Ar is 2,4,6-trichlorophenyl, $R^1$, $R^2$ and $R^3$ are methyl and $n$ is 2) as a beige solid, m.p. 86-88°C.

By a procedure similar to that of Example 4, the hydrazide product prepared above was chlorinated with phosphorus pentachloride to give the hydrazone disulfide product of the formula

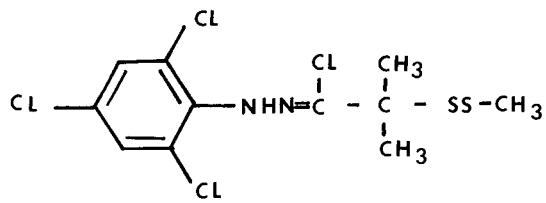

Elemental analysis for $C_{11}H_{12}Cl_4N_2S_2$ showed: %S, calc. 17.0, found 17.1; %Cl, calc. 37.5, found 40.9.

By a procedure similar to that of Examples 1–5, other compounds of Formula (I) were prepared. These compounds and the compounds of Examples 1–5 are tabulated in Table II.

Example 6

Insect Control

The compounds tabulated in Table II were tested as juvenile hormonal mimetic insecticides by the following procedures.

Cabbage Looper (*Trichoplusia ni*)

5 microliters of an acetone solution containing a certain concentration micrograms of the test compound were applied topically to the entire length of the body of a late-fifth-stage cabbage looper larva. Normally 10 larvae were treated per test. The treated larvae were then fed until they pupated. The pupae were then incubated until the adult emerged. The mortality of the pupae and adults was determined. The compounds tested, the concentration (mcg/insect) and the total pupal and adult mortality are tabulated in Table III.

Alfalfa Weevil (*Hapera postica Gyllenhal*)

Alfalfa weevil larvae were tested by the same procedure employed for cabbage looper. The compounds tested, the concentration (mcg/insect) and the total pupal and adult mortality are tabulated in Table IV.

Yellow Mealworm (*Tenebrio molitor*)

About two-day-old yellow mealworm pupae were tested by the same procedure employed for cabbage looper. The compounds tested, the concentration (mcg/insect) and the total pupal and adult mortality are tabulated in Table V.

Kissing Bug (*Rhodnius prolixus*)

Late-fifth-stage kissing bug numphs (24 hours after a blood meal) were tested by the same procedure employed for cabbage looper. The compounds tested, the concentration (mcg/insect) and the total larval, pupal and adult mortality are tabulated in Table VI.

TABLE II

| No. | Ar | $R^1$ | $R^2$ | $R^3$ | n |
|---|---|---|---|---|---|
| 1 | 2,4,6—$Cl_3\phi$ | $CH_3$ | $CH_3$ | $CH_3$ | 3 |
| 2 | " | $CH_3$ | $CH_3$ | $t$—$C_4H_9$ | 3 |
| 3 | " | $CH_3$ | $CH_3$ | $C_2H_5$ | 2,3 |
| 4 | " | $CH_3$ | $CH_3$ | $CH_3$ | 1 |
| 5 | " | $CH_3$ | $CH_3$ | $CH_3$ | 2 |
| 6 | " | H | H | $CH_3$ | 1 |
| 7 | " | H | H | —$CCL_3$ | 2 |
| 8 | " | H | H | $CH_3$ | 2 |
| 9 | " | H | H | $i$—$C_3H_7$ | 2 |
| 10 | " | H | $CH_3$ | $CH_3$ | 2 |
| 11 | " | H | $CH_3$ | $CH_3$ | 1 |
| 12 | " | H | $CH_3$ | —$CCl_2CCl_2H$ | 2 |
| 13 | " | $CH_3$ | $CH_3$ | 4—$Cl\phi$ | 2 |

TABLE III

Cabbage Looper Control

| Compound No. | Concentration | % Mortality |
|---|---|---|
| 1 | 1 | 100 |
| 2 | 0.4 | 90 |
| 3 | 100 | 100 |
| 4 | 100 | 100 |
| 5 | 100 | 100 |
| 6 | 0.4 | 90 |
| 7 | 100 | 60 |
| 8 | 1.3 | 90 |
| 9 | 1.2 | 90 |
| 10 | 100 | 100 |
| 11 | 100 | 100 |
| 12 | 100 | 10 |
| 13 | 1 | 90 |

TABLE IV

Alfalfa Weevil Control

| Compound No. | Concentration | % Mortality |
|---|---|---|
| 1 | 0.3 | 100 |
| 2 | 0.14 | 90 |
| 3 | 0.14 | 90 |
| 4 | 0.38 | 90 |
| 5 | 0.14 | 90 |
| 6 | 0.3 | 90 |
| 7 | 5 | 40 |
| 8 | 1.5 | 90 |
| 9 | 5 | 100 |
| 10 | 0.3 | 90 |
| 11 | 1.6 | 90 |
| 12 | 5 | 10 |
| 13 | 0.46 | 90 |

TABLE V

Yellow Mealworm Control

| Compound No. | Concentration | % Mortality |
|---|---|---|
| 1 | 10 | 100 |
| 2 | 10 | 20 |
| 3 | 10 | 100 |
| 4 | 1.6 | 90 |
| 5 | 2.1 | 90 |
| 6 | 3.7 | 90 |
| 7 | 10 | 0 |
| 8 | 4.6 | 90 |
| 9 | 10 | 90 |
| 10 | 10 | 90 |
| 11 | 2.1 | 90 |

TABLE VI

Kissing Bug Control

| Compound No. | Concentration | % Mortality |
|---|---|---|
| 1 | 10 | 90 |
| 2 | 10 | 60 |
| 3 | 10 | 100 |

TABLE VI-continued

| Compound No. | Kissing Bug Control Concentration | % Mortality |
|---|---|---|
| 4 | 3.2 | 90 |
| 5 | 3.6 | 90 |
| 6 | 7 | 90 |
| 7 | 10 | 10 |
| 8 | 10 | 0 |
| 9 | 10 | 0 |
| 10 | 10 | 90 |
| 11 | 6.5 | 90 |

What is claimed is:

1. A method for inhibiting the normal growth pattern of insects which comprises contacting pre-adult insects with a metamorphosis-inhibiting amount of a compound of the formula

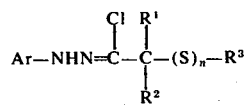

wherein $R^1$ is hydrogen or alkyl of 1 to 6 carbon atoms, $R^2$ is hydrogen or alkyl of 1 to 6 carbon atoms, $R^3$ is alkyl of 1 to 6 carbon atoms, haloalkyl of 1 to 6 carbon atoms containing 1 to 5 fluoro, chloro or bromo atoms or phenyl substituted with up to 3 fluoro, chloro or bromo atoms, Ar is phenyl substituted with up to 5 fluoro, chloro or bromo atoms and $n$ is 1, 2 or 3.

2. The method of claim 1 wherein $R^1$ is hydrogen.

3. The method of claim 1 wherein $R^1$ is alkyl of 1 to 3 carbon atoms and $R^2$ is alkyl of 1 to 3 carbon atoms.

4. The method of claim 3 wherein $R^3$ is alkyl of 1 to 6 carbon atoms or chloroalkyl of 1 to 2 carbon atoms containing 1 to 5 chloro atoms.

5. The method of claim 4 wherein $R^3$ is alkyl of 1 to 6 carbon atoms.

6. The method of claim 5 wherein Ar is phenyl substituted with up to 5 chloro or bromo atoms.

7. The method of claim 5 wherein Ar is phenyl substituted with up to 5 chloro atoms.

8. The method of claim 5 wherein Ar is 2,4,6-trichlorophenyl.

9. The method of claim 8 wherein $R^1$, $R^2$ and $R^3$ are methyl.

10. The method of claim 8 wherein $R^1$ and $R^2$ are methyl and $R^3$ is t-butyl.

11. The method of claim 8 wherein $R^1$ and $R^2$ are methyl and $R^3$ is ethyl.

12. The method of claim 9 wherein $n$ is 1.

13. The method of claim 10 wherein $n$ is 3.

14. A composition comprising a metamorphosis-inhibiting amount of a compound of the formula

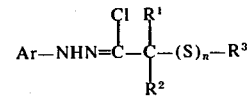

wherein $R^1$, $R^2$, $R^3$, Ar and $n$ are as defined in claim 1, and a biologically inert carrier.

15. The composition of claim 14 wherein $R^1$ is hydrogen.

16. The composition of claim 14 wherein $R^1$ is alkyl of 1 to 3 carbon atoms and $R^2$ is alkyl of 1 to 3 carbon atoms.

17. The composition of claim 16 wherein $R^3$ is alkyl of 1 to 6 carbon atoms or chloroalkyl of 1 to 2 carbon atoms containing 1 to 5 chloro atoms.

18. The composition of claim 17 wherein $R^3$ is alkyl of 1 to 6 carbon atoms.

19. The composition of claim 18 wherein Ar is phenyl substituted with up to 5 chloro or bromo atoms.

20. The composition of claim 18 wherein Ar is phenyl substituted with up to 5 chloro atoms.

21. The composition of claim 18 wherein Ar is 2,4,6-trichlorophenyl.

22. The compopsition of claim 21 wherein $R^1$, $R^2$ and $R^3$ are methyl.

23. The composition of claim 21 wherein $R^1$ and $R^2$ are methyl and $R^3$ is t-butyl.

24. The composition of claim 21 wherein $R^1$ and $R^2$ are methyl and $R^3$ is ethyl.

* * * * *